United States Patent
Shimomura et al.

(10) Patent No.: US 11,195,610 B2
(45) Date of Patent: Dec. 7, 2021

(54) PRIORITY ALERTS BASED ON MEDICAL INFORMATION

(71) Applicants: Takuya Shimomura, Cary, NC (US); William Lacy, Garnet Valley, PA (US)

(72) Inventors: Takuya Shimomura, Cary, NC (US); William Lacy, Garnet Valley, PA (US)

( * ) Notice: Subject to any disclaimer, the term of this patent is extended or adjusted under 35 U.S.C. 154(b) by 228 days.

(21) Appl. No.: 15/821,173

(22) Filed: Nov. 22, 2017

(65) Prior Publication Data
US 2019/0156937 A1    May 23, 2019

(51) Int. Cl.
| | |
|---|---|
| G06K 9/00 | (2006.01) |
| G16H 30/40 | (2018.01) |
| G16H 40/20 | (2018.01) |
| G16H 10/40 | (2018.01) |
| G16H 50/20 | (2018.01) |
| G16H 50/30 | (2018.01) |
| H04L 12/58 | (2006.01) |
| H04L 12/18 | (2006.01) |

(52) U.S. Cl.
CPC .......... *G16H 30/40* (2018.01); *G16H 10/40* (2018.01); *G16H 40/20* (2018.01); *G16H 50/20* (2018.01); *G16H 50/30* (2018.01); *H04L 12/1895* (2013.01); *H04L 51/26* (2013.01)

(58) Field of Classification Search
None
See application file for complete search history.

(56) References Cited

U.S. PATENT DOCUMENTS

| | | | |
|---|---|---|---|
| 7,974,924 B2 | 7/2011 | Holla et al. | |
| 9,763,071 B2 | 9/2017 | Balram et al. | |
| 9,785,748 B2 | 10/2017 | Koo et al. | |
| 2004/0122709 A1 | 6/2004 | Avinash et al. | |
| 2008/0021834 A1* | 1/2008 | Holla | G06F 21/602 |
| | | | 705/51 |
| 2013/0209068 A1* | 8/2013 | Lynn | G16H 40/60 |
| | | | 386/278 |
| 2015/0317337 A1 | 11/2015 | Edgar | |
| 2016/0142894 A1 | 5/2016 | Papakonstantinou et al. | |
| 2016/0350919 A1* | 12/2016 | Steigauf | G06T 7/0014 |
| 2017/0024547 A1* | 1/2017 | Bidani | G06F 16/248 |
| 2017/0300654 A1 | 10/2017 | Stein et al. | |
| 2018/0078231 A1* | 3/2018 | Butani | A61B 6/5217 |
| 2019/0313903 A1* | 10/2019 | McKinnon | G16H 50/20 |

* cited by examiner

*Primary Examiner* — Sean M Conner
(74) *Attorney, Agent, or Firm* — Heslin Rothenberg Farley & Mesiti P.C.

(57) ABSTRACT

A method and apparatus are disclosed herein for generating and sending priority alert notifications based on medical information, such as, for example, medical information obtained from analyzing medical images. In one embodiment, the method comprises: determining, using an image analysis engine, whether one or more features in a medical image of a patient meet predefined criteria, the predefined criteria being indicative of a medical condition; determining, using the image analysis engine, whether an alert notification is to be sent regarding results of determining whether the one or more features in the medical image meet the predefined criteria; and sending the alert notification with indicia indicative of a priority level if the one or more features in the medical image meet the predefined criteria, including sending medical information that prompted the image analysis engine to send the notification at the priority level.

28 Claims, 9 Drawing Sheets

Text Message
701

Image Slice
(e.g., snapshot)
702

Send an indication to the AI engine that the medical image has been received by a medical information management system and is available for analyzing by the AI engine
801

Determine whether features in a medical image of a patient meet predefined criteria and optionally other information (e.g., information related to the medical condition), where the predefined criteria are indicative of a medical condition
802

Determine whether an alert notification is to be sent
803

Select the indicia indicative of the priority level to use for the notification based on an urgency with respect to the medical condition of the patient
804

Send the alert notification with the indicia indicative of the priority level, including medical information that prompted the sending of the notification at the priority level
805

Present the alert notification in a display
806

FIG. 8

PRIORITY ALERTS BASED ON MEDICAL INFORMATION

FIELD OF THE INVENTION

Embodiments of the present invention relate to the field of medical imaging analysis; more particularly, embodiments of the present invention relate to automatically generating alert notifications after analysis of medical images indicates that a patient has a medical condition that needs urgent attention by a medical professional.

BACKGROUND

Current medical imaging technology includes the use of medical images such as, among others, x-rays, mammograms, computerized tomography (CT) scans, magnetic resonance images (MRIs), positron emission tomography (PET) scans and ultrasound images. These images are generated by medical imaging modalities.

Medical facilities are more readily adopting electronic displays for displaying medical images. Often after an imaging modality takes medical images, those images are included in a study that is sent to a picture archiving and communication system (PACS). The PACS is a medical imaging technology that allows access to images from multiple locations. Doctors and/or other medical professionals obtain studies that are stored in the PACS and review, or read, the images in the studies to obtain clinical information about their patients. If a patient has a serious medical condition that needs urgent attention, the doctor is often able to make that determination by reviewing the images in the study.

Unfortunately, because doctors have large numbers of patients, an individual doctor may have a large number of studies to review and thus may not be able to know which of their patients have an urgent medical condition until all the images from all the studies have been reviewed. Therefore, without knowing which studies to prioritize, it's possible that the lengthy process of reviewing the studies will mean that a patient with a serious medical condition won't receive urgent medical care or such care will be delayed, leading to negative consequences for the patient.

SUMMARY OF THE INVENTION

A method and apparatus are disclosed herein for generating and sending priority alert notifications based on medical information, such as, for example, medical information obtained from analyzing medical images. In one embodiment, the method comprises: determining, using an image analysis engine, whether one or more features in a medical image of a patient meet predefined criteria, the predefined criteria being indicative of a medical condition; determining, using the image analysis engine, whether an alert notification is to be sent regarding results of determining whether the one or more features in the medical image meet the predefined criteria; and sending the alert notification with indicia indicative of a priority level if the one or more features in the medical image meet the predefined criteria, including sending medical information that prompted the image analysis engine to send the notification at the priority level.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIG. 8 is a flow diagram of one embodiment of a process for generating medical alert notifications.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

A method and apparatus disclosed herein provide an early alert notification to a doctor or other medical professional as to a potentially urgent medical condition of a patient. In one embodiment, the alert notification is provided with priority information, which allows for faster identification of medical image that should be reviewed by a doctor. In one embodiment, the alert notification is accessible at a remote location, via a medical image management system or a mobile device. In one embodiment, the alert notification is accessible through chat and/or other mobile applications.

In one embodiment, analysis is automatically performed on a new medical image. In one embodiment, this automatic analysis is run with artificial intelligence (AI) technology. Depending on the result of the analysis, an emergency alert is automatically sent to one or more doctors or medical professionals. In one embodiment, the determination as to whether to send this alert is handled automatically using the AI technology. In this manner, a doctor with many medical images (or studies) to be reviewed is able to quickly identify those that needs immediate attention.

Figure 1:
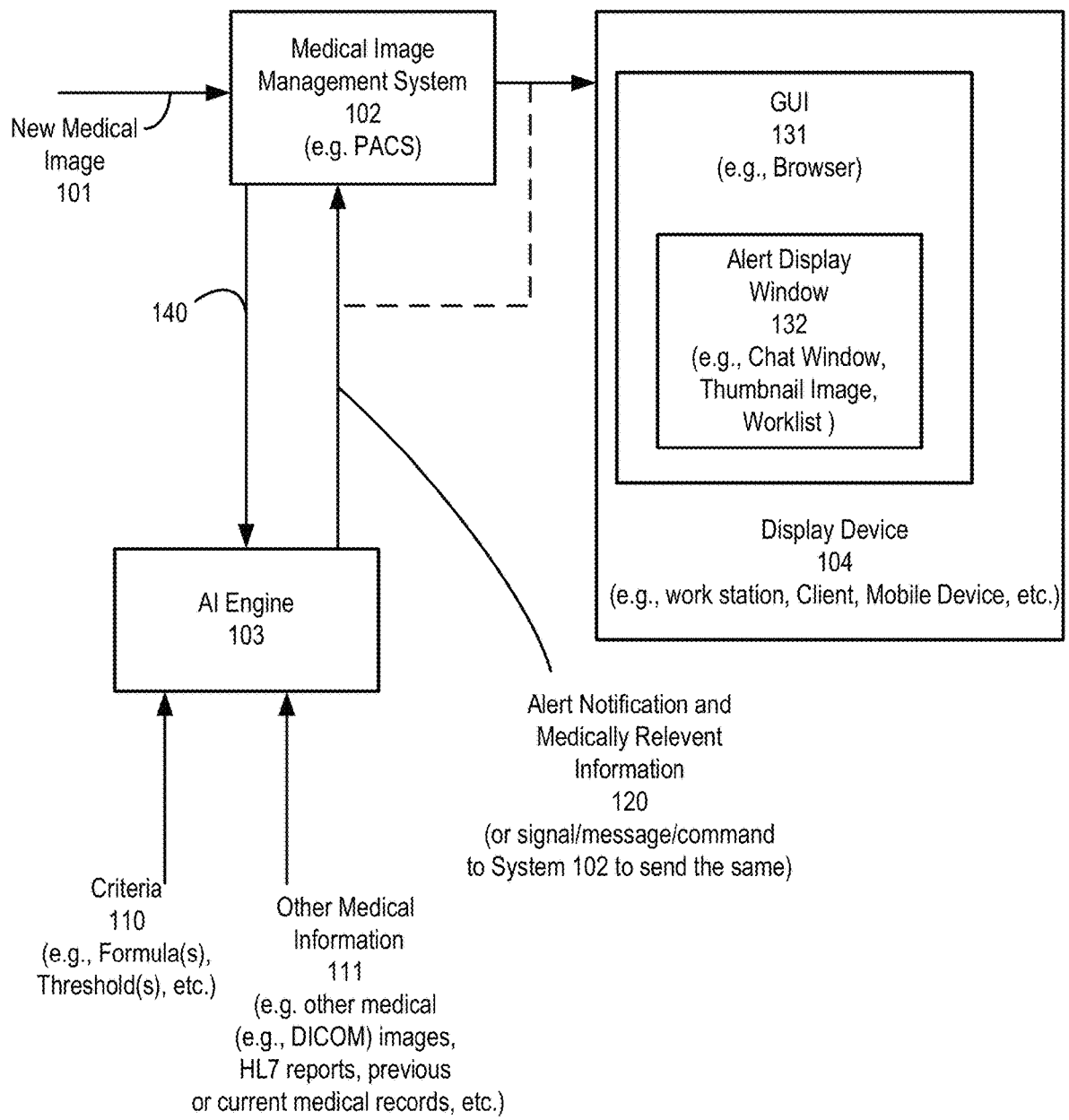
FIG. 1 is a data flow diagram of one embodiment of an alert notification process.

FIG. 1 is a data flow diagram of one embodiment of an alert notification process. Referring to FIG. 1, a new medical image 101 of a patient is received by a medical image management system 102. In one embodiment, medical image 101 is sent from a medical imaging modality that performs medical imaging (e.g., X-ray radiography, magnetic resonance imaging, ultrasound, endoscopy, tactile imaging, thermography, nuclear medicine functional imaging techniques such as positron emission tomography (PET) and single-photon emission computed tomography (SPECT), etc.). Medical image management system 102 allows medical images to be accessed and revised by individuals. In one embodiment, medical image management system 102 comprises a picture archiving and communication system (PACS).

After medical image 101 has been received by medical image management system 102, artificial intelligence (AI)

engine 103 obtains medical image 101 and automatically performs a read of medical image 101 to obtain clinical information, or findings. In one embodiment, AI engine 103 uses artificial intelligence to access the information present in a medical image, such as medical image 101, to determine if the patient has a medical condition for which an alert notification should be sent to a doctor or other medical professional. In one embodiment, AI engine 103 comprises a combination of hardware (e.g., one or more processing cores or processors) and software. In another embodiment, AI engine 103 comprises a combination of hardware (e.g., one or more processing cores or processors), software and firmware. In other embodiments, AI engine 103 comprises only hardware. In one embodiment, AI engine 103 is a server.

In one embodiment, AI engine 103 performs the reading of medical image 101, obtains the clinical information for medical image 101, and generates an alert notification (as described in more detail below) without human intervention. That is, a physician or other medical professional does not perform any of the decision making process when medical image 101 is being reviewed to determine whether the patient's medical condition warrants and that alert notification be made available or is sent.

In one embodiment, AI engine 103 obtains medical image 101 after being notified the medical image 101 has been received by medical image management system 102. In one embodiment, AI engine 103 is notified by one or more messages, signals, commands from medical image management system 102. In another embodiment, AI engine 103 is notified by the modality that medical image 101 has been sent to medical image management system 102. The notification is received on a receive communication interface of AI engine 103.

In one embodiment, AI engine 103 obtains medical image 101 by accessing medical image management system 102. In another embodiment, medical image management system 102 sends medical image 101 to AI engine 103. In one embodiment, AI engine 103 runs constantly and waits for new studies (with medical images) to arrive, and when they do, AI engine 103 immediately reviews them for medical conditions (e.g., life threatening issues), prioritizes them, and alerts medical professionals accordingly. Note that while AI engine 103 is shown separate from medical image management system 102, in one embodiment, AI engine 103 is part of medical image management system 102.

After receiving medical image 101, AI engine 103 obtains features of medical image 103 and performs analysis on those features to obtain or determine clinical information. In one embodiment, the analysis performed by AI engine 103 includes applying criteria 110 to the image features to determine if the medical condition of the patient shown in medical image 101 indicates that an alert notification should be sent to one or more medical professionals and the priority level that should accompany such an alert. In one embodiment, criteria 110 comprise a formula that uses data from the image features obtained by AI engine 103 from medical image 101, or derived from the image features, to determine if an alert notification is warranted as well as its priority level. In one embodiment, the formula includes threshold comparisons between data from the image features and predetermined values to determine if an alert notification is warranted and its priority level. In one embodiment, criteria 110 is provided by one or more individuals (e.g., one or more doctors or other medical professionals). In another embodiment, criteria 110 is provided by a medical facility (e.g., hospital). This may be in response to a doctor's request or instruction. In one embodiment, criteria 110 that is employed is selected based on the situation at the medical facility or office. For example, there may be one set of criteria for day-to-day operation and another set of criteria if in a triage situation.

In one embodiment, AI engine 103 determines whether an alert notification is necessary and its priority level by using image features of medical image 101 and other medical information, such as medical information 111. Medical information 111 may include one or more other medical images (e.g., DICOM images), medical reports (e.g., an HL7 report), or current or past medical records of the patient or other patients (e.g., family histories).

As a result of applying criteria 110, if AI engine 103 determines that an alert notification is needed, AI engine 103 sends alert notification 120. In one embodiment, AI engine 103 sends alert notification 120 to medical image management system 102, which then forwards it to or makes it accessible by a user (e.g., a doctor or other medical professional, patient, etc.). In an alternative embodiment, AI engine 103 sends alert notification 120 to, or makes it accessible, directly by a user (e.g., a doctor or other medical professional, patient, etc.).

In one embodiment, alert notification 120 includes a priority level indication. In one embodiment, the priority level indication specifies the urgency level of the medical condition of the patient as determined by AI engine 103 as a result of applying criteria 110. The priority level indication may be specified using indicia that is to be displayed to a user receiving or accessing the alert notification. Such indicia may include different colored graphical user interface elements (e.g., boxes, shapes, etc.) that signify the different levels of priority for the different levels of urgency. Alternatively, in one embodiment, different colors are used in the alert notification to specify different levels of priority (e.g., red equals very urgent, while green equals no urgency).

In one embodiment, alert notification 120 also includes medical information that is medically relevant to the determination made by AI engine 103 to send the alert notification. This medically relevant information may include image features (e.g., raw image data) or information derived from such features (e.g., a measurement derived from the size of an image feature). For example, if AI engine 103 determines that one of the image features (or information derived therefrom) indicates that the patient has a particular medical condition, the medically relevant information sent with alert notification 120 includes that image feature (or information derived therefrom). In one embodiment, the medically relevant information that is sent by AI engine 103 includes an image slice with one or more parts of the image highlighted to enable an individual viewing the image to quickly focus in on the relevant part(s) of the image. In one embodiment, the image slice is a snapshot, such as set forth in U.S. patent application Ser. No. 14/736,550, entitled "Methods and Apparatus for Obtaining a Snapshot of a Medical Imaging Display," filed Jun. 11, 2015.

In one embodiment, AI engine 103 also generates an ordering of one or more specific additional tests based on the results of analysis. In one embodiment, such information it sent as part of the alert notification and/or is sent to a medical facility that can administer or cause the performance of such tests. For example, if as the result of analyzing an electrocardiogram (EKG) and a weak signal is detected, AI engine 103 alerts the medical staff that a shock needs to be performed on the patient (before the patient has a cardiac arrest). In this case, the instruction from AI engine 103 is generated as a result of reviewing past EKGs of the patient or performing a real-time comparison between the patient's current EKG and those of past patients who have had a cardiac arrest and determining a commonality between the patient and other patients that led to cardiac arrest condition.

In an alternative embodiment, AI engine 103 does not send alert notification 120 itself, but causes alert notification 120 to be sent or made accessible. For example, AI engine 103 may send instructions to medical image management system 102 to send or make accessible alert notification 120. In such a case, AI engine 103 provides or specifies the medically relevant information to be included in alert notification 120.

In one embodiment, an individual is able to receive the alert notification sent by AI engine 103 by viewing alert notification 120 on a display device 104. In one embodiment, display device 104 is part of a workstation or client computer system. In another embodiment, display device 104 is part of a mobile device (e.g., tablet, mobile phone, personal digital assistant, watch, a wearable device, etc.).

In one embodiment, alert notification 120 is displayed in a graphical user interface (GUI) (e.g., browser or display device 104). The GUI includes an alert notification display window (e.g., a chat or other messaging window, a window for displaying a log (e.g., a thinklog), worklist, etc.).

Note that the techniques described herein are not limited to using an AI engine to perform medical image analysis and generate alert notifications. Other image analysis engines may be used. For example, in one embodiment, an image analysis engine comprises a computer aided diagnosis based image analyzer. Other image analysis engines such as those comprised of hardware, software and/or firmware may be configured to analyze medical images and/or other medical information and determine whether an alert notification should be generated and sent, along with a priority level. Thus, while the detailed description uses an AI engine for such image and medical information analysis, it should be understood that the AI engine could be replaced with another medical image and information analysis engine. This should help to avoid obscuring the present invention.

FIGS. 2-7 illustrate embodiments of alert notifications in the context of an example of a medical image of a patient with possible brain stroke that results from the patent being scanned and the image being sent to a medical image management system (e.g., a PACS server, etc.). In one embodiment, the medical image is newly acquired from an imaging modality or from an image repository and is immediately read by an AI engine before a human doctor opens up the image and reviews it. In one embodiment, the AI engine is on the server that receives the medical image and accesses the medical image for analysis when the image is received by the server.

In this example, the AI engine obtains findings, or clinical information, such as, for example, existence of hemorrhage, position in the brain, volume of hemorrhage or existence of midline shift, when it reads the medical image (without doctor intervention in the reading of the medical image). Based on the information the AI engine obtains from the image, the AI engine determines a level of urgency or prioritization that should be assigned, if any, to a notification that is to be made regarding the findings made by the AI engine, whether that recipient of the alert notification is one or more doctors, other medical professionals, or a medical facility (e.g., a hospital, clinic, etc.). In one embodiment, a hospital (or other medical facility) and/or a doctor(s) define the level of urgency to be informed from the AI engine. In one embodiment, the level of prioritization is defined by setting the criteria or formula that comprises one or more features or elements that the AI engine obtains from reading the medical image. For example, in the case of the stroke example, these features may include the size of hemorrhage or existence of midline shift.

In one embodiment, the AI engine is configured to review additional information based on whether the medical condition (e.g., trauma) being experienced is a first occurrence or a repeat of such a condition. In such a case, the AI engine is configured to review past medical histories to make a determination as to how often a patient has such a condition and generates an alert notification with a particular priority if the condition and the frequency of its occurrence warrants a particular level of priority. Such a priority may be specified by a doctor or medical facility.

Figure 2:
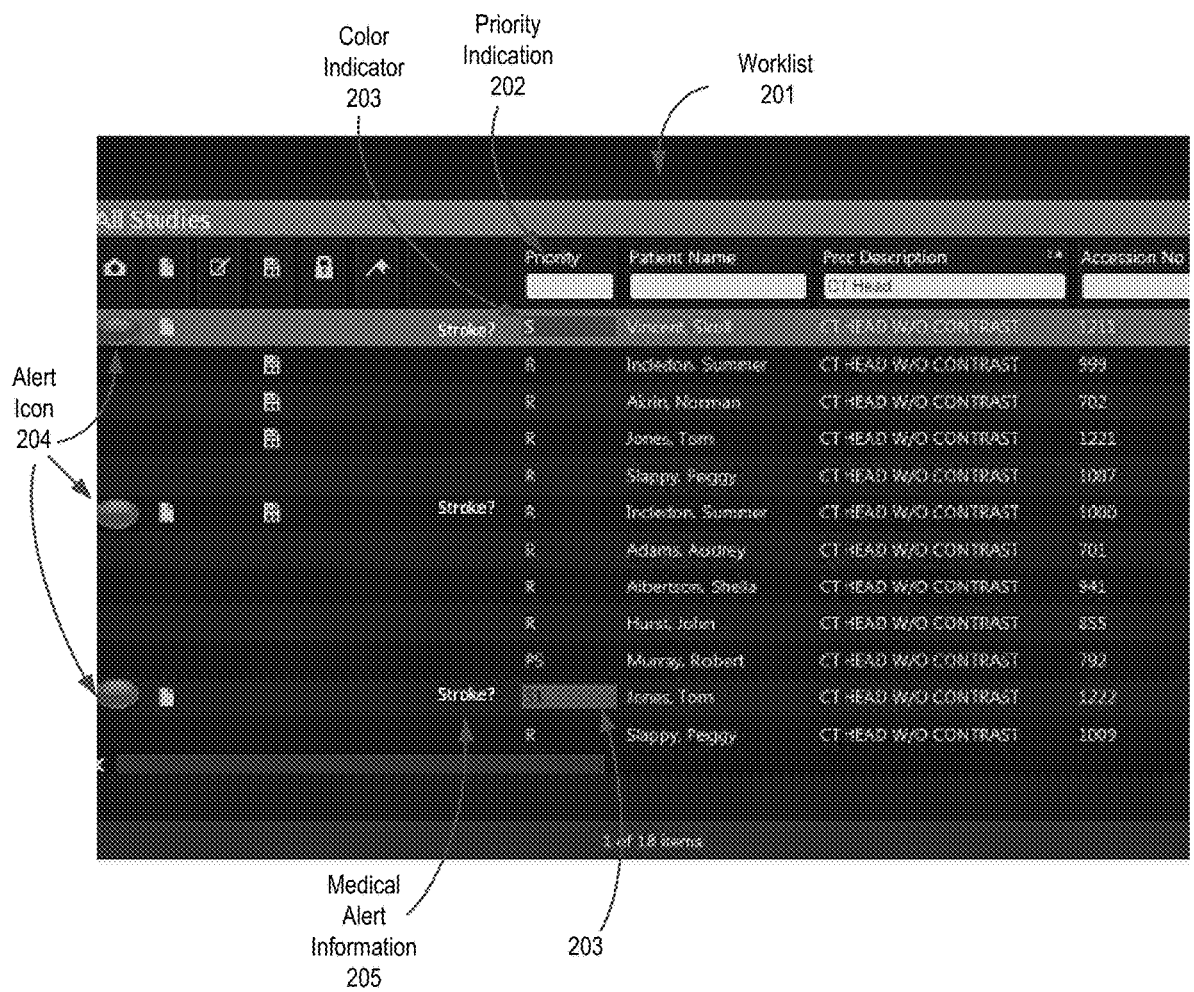
FIG. 2 illustrates one embodiment of a work list.

In one embodiment, the alert notification is in the form of an eye-catching color (e.g., different colors for different priority levels/urgencies), icon or another method that can be defined later on a worklist. FIG. 2 illustrates one embodiment of a work list. The work list may be generated by software running on a medical image management system that provides doctors and other medical personnel access to medical information such as studies, reports, and images. Referring to FIG. 2, worklist 201 includes a list of studies and individual images. In one embodiment, worklist 201 includes a priority indication column 202. As shown, priority indication column 202 specifies a priority level associated with each of the items in worklist 201. Two of the items listed in priority indication column 202 have a color indicator 203 that is used to specify the priority level (e.g., red is very urgent, and no color means no urgency). In alternative embodiments, other types of indicators are used, including, for example, other graphical user interface elements such as icons, shapes, patterns, etc. Thus, a doctor working at a work station (e.g., client computer system, mobile device, etc.) can be notified of the urgency that the AI engine has specified and indicated on worklist 201.

In one embodiment, worklist 201 also includes alert icons 204 on some of the list items that, based on their color, alert the viewer that there is image that has a certain priority level of urgency. In this case, three of the list items have such an icon in a color (e.g., red) that indicates it's very urgent.

In one embodiment, worklist 201 also includes a column specifying medical alert information 205 that is information that the AI engine determined from its review of the image features. In this example given, medical alert information 205 indicates that the AI engine has determined that the features of the image may indicate a potential stroke.

Figure 3:
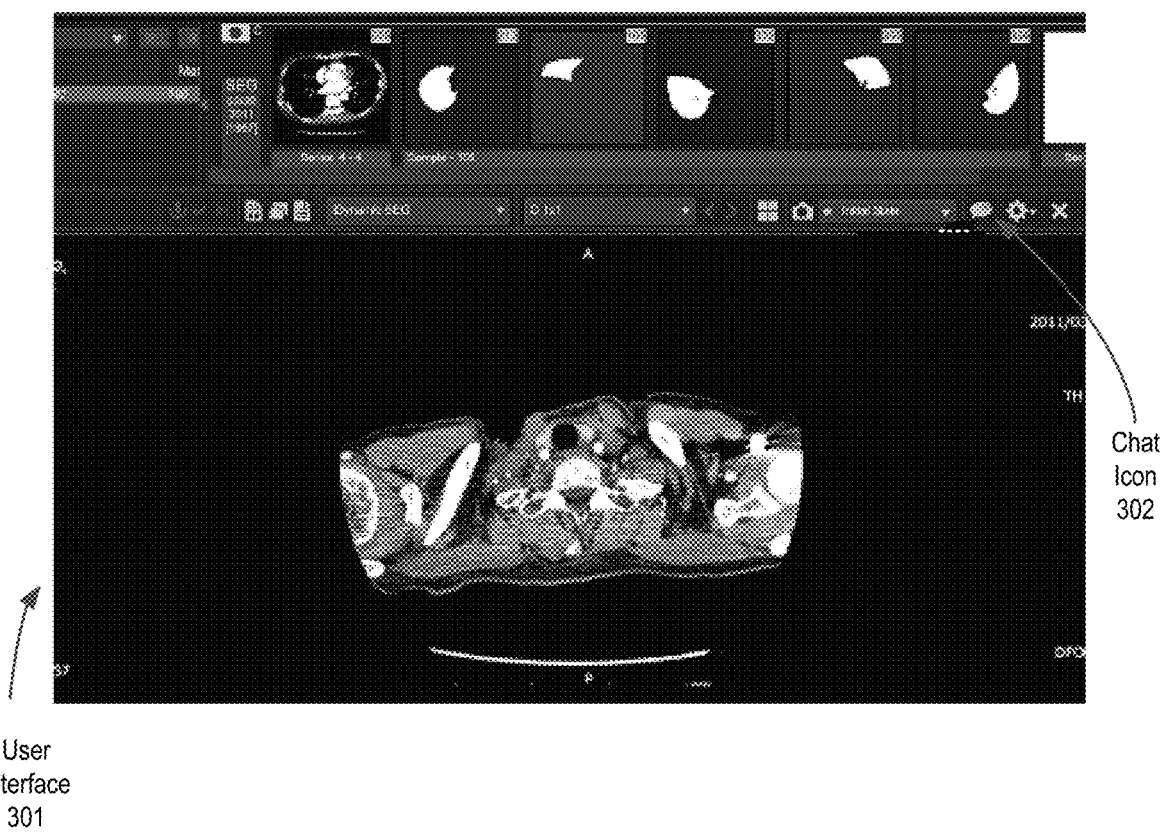
FIG. 3 illustrates another embodiment of a user interface with another type of notification.

FIG. 3 illustrates another embodiment of a user interface with another type of notification. Referring to FIG. 3, user interface 301 includes a chat icon 302. In one embodiment, chat icon 302 is part of a thinklog interface, such as set forth in U.S. patent application Ser. No. 14/820,144, entitled "Methods and Apparatus for Logging Information Using a Medical Imaging Display System," filed Aug. 6, 2015. In one embodiment, when chat icon 302 changes, a viewer is notified that an alert notification has been received. In one embodiment, the change to chat icon 302 that notifies the viewer that an alert notification has been received is a change in color for at least a portion of the icon. Thus, a doctor or other medical professional at a display device (e.g., a work station, client computer system, mobile device, etc.) can be notified of an alert by the change in color. However, in alternative embodiments, other changes may indicate that an alert notification has been received is, such as, for example, changes in shape, size, pattern fill, etc., are used.

In one embodiment, the user interface of the display device is such that information may be provided without opening or reading the image. Thus, in one embodiment, a medical professional (e.g., a doctor) at a display device (e.g., a work station, client computer system, mobile device, etc.) can be provided one or more of the following without yet opening and reading the image:

(a) if urgent or not;
(b) a level of urgency;
(c) findings that that the AI engine has determined as a result of reading a medical image (and that are used to define the level of urgency); and
(d) a snapshot or portion of a medical image where the AI engine has identified the features that led to the findings.

In one embodiment, one or more of the above is displayed on the interface in response to performing a mouseover event on a portion of the user interface. For example, by moving a cursor with a computer mouse over a button or other graphical user interface element being displayed, the findings made by the AI engine and/or the snapshot is displayed on the display screen on which the user interface appears.

Figure 4:
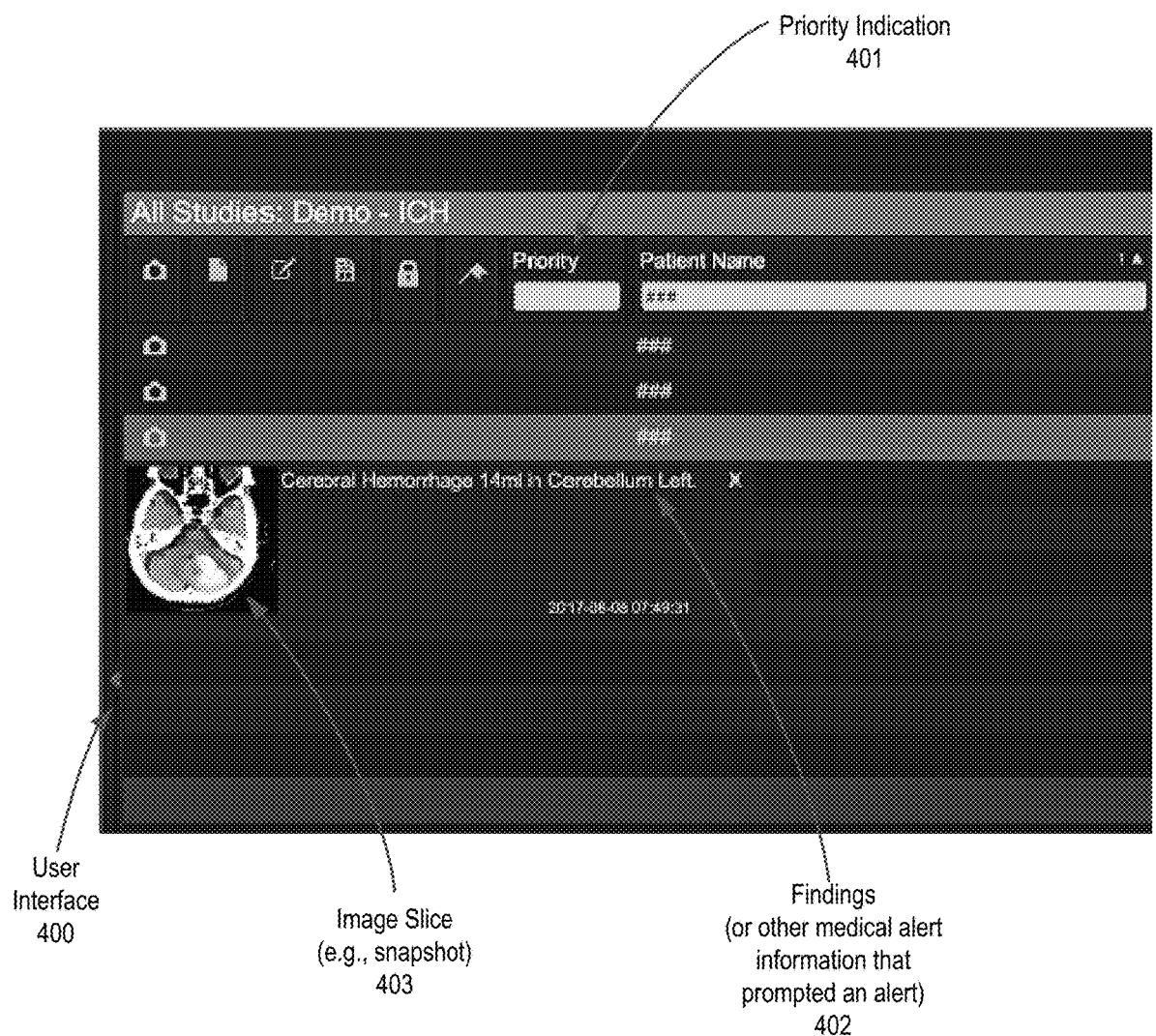
FIG. 4 illustrates an example of one embodiment of a user interface.

FIG. 4 illustrates an example of one embodiment of a user interface. Referring to FIG. 4, user interface 400 includes priority indication 401 to specify the entry in the worklist is urgent or not, where its color indicates its level of urgency. User interface 400 also includes findings (or other medical alert information that prompted the alert notification) 402, along with an image slice (e.g., snapshot) 403 highlighting the portion of the medical image having the features that the AI engine identified that led to the AI engine issuing (or causing) the alert notification.

Figure 5:
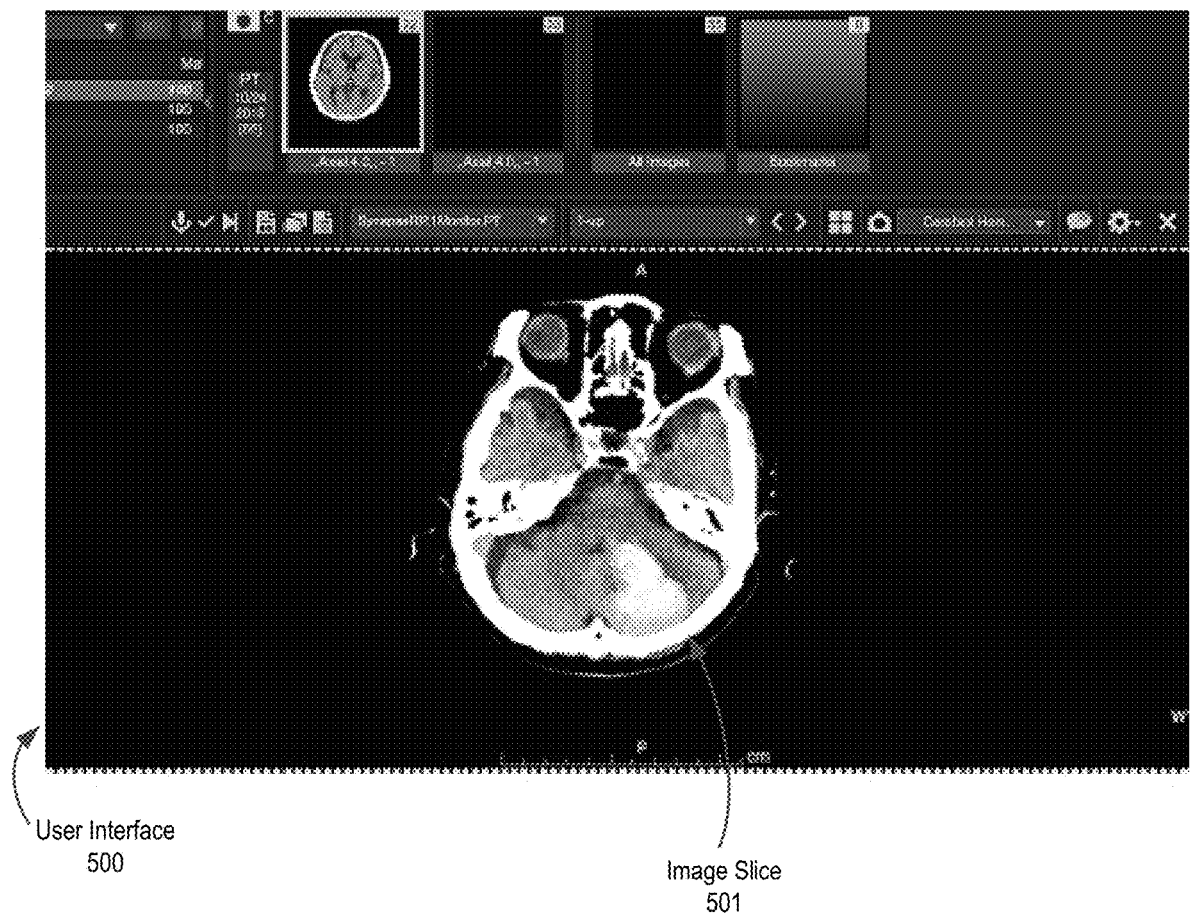
FIG. 5 illustrates one embodiment of a user interface displaying an image slice.

Once a medical professional (e.g., doctor) is notified of the urgency, if that person decides to open the image, in one embodiment, he/she can use the snapshot that is shown on the worklist to directly open to the image slice where the AI engine has detected important finding or features. In one embodiment, this occurs without having to scroll through a number of other images in a study to get to that particular image slice. FIG. 5 illustrates user interface 500 displaying image slice 501.

Note that the user interface is not limited to being displayed on a work station. In one embodiment, a user may receive and/or an alert notification on a mobile device (e.g., a mobile phone, a tablet (e.g., iPad), a portable computer system, etc.). In one embodiment, the alert notification is displayed in a chat window. Thus, in such a case, a medical professional not working at a workstation, yet having their mobile device, can be notified of the urgency that the AI engine has detected via the chat window.

Figure 6:
FIG. 6 illustrates one embodiment of a chat window.

FIG. 6 illustrates an example of a chat window. Referring to FIG. 6, chat window 601 displays an alert notification element 620. By selecting alert notification element 620, the chat window on the right side of chat window 601 is displayed that includes medical image 610 (e.g., a snapshot) with highlighting to indicate the portion of the medical image having the features that the AI engine identified that led to the AI engine issuing the alert notification. Also shown in the chat window is medical alert information 611 (other than the image) that indicates why the AI engine made a determination to cause the alert notification to be sent (and which is used to define the level of urgency). Such information may include the findings or other information corresponding to the medical rationale behind the alert notification. In one embodiment, chat window 601 is part of a thinklog, such as set forth in U.S. patent application Ser. No. 14/820,144, entitled "Methods and Apparatus for Logging Information Using a Medical Imaging Display System," filed Aug. 6, 2015.

Chat window 601 also includes a text entry area 602 to enable an individual to add one or more text messages into the chat window for sharing among the chat participants.

In one embodiment, multiple parties or medical professionals (e.g., doctors) can be notified of the urgency at the same time. In one embodiment, the notification of multiple parties is performed by sending a broadcast chat message from the AI engine. Alternatively, this broadcast chat message is sent from a medical image management system. In one embodiment, the chat window is available to a medical professional on their work station and their mobile device, so that they have accessibility from either of the devices.

Figure 7:
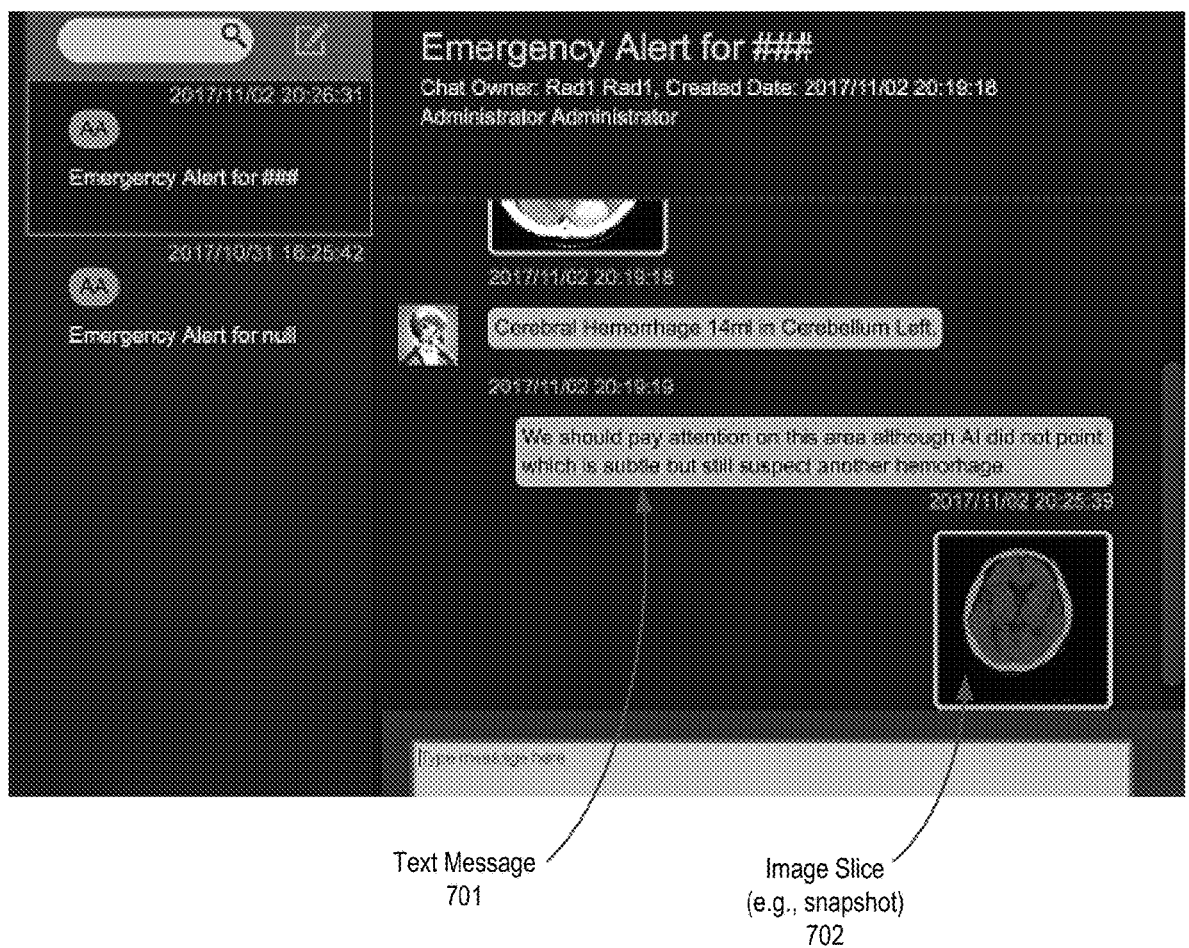
FIG. 7 illustrates another view of the chat window of FIG. 6.

In one embodiment, a medical professional is able to access the medical information associated with the alert notification. For example, once a doctor is notified the urgency and decides to open the image, the doctor can view the image slice (e.g., snapshot) in the chat window. In this matter, the medical professional can view the image slice where the AI engine has detected important findings without doing any scrolling through a number of other images to get to that particular slice. FIG. 7 illustrates another view of the chat window of FIG. 6. Referring to FIG. 7, the chat window displays a text entry that enables an individual to add text message 701 to the chat. In one embodiment, an individual is also able to add one or more additional images, such as, for example, image slice 702 (e.g., a snapshot) to the chat. In this way, individuals in the chat can communicate and exchange their findings using text or snapshots/image slices that they newly create on the viewer.

FIG. 8 is a flow diagram of one embodiment of a process for generating medical alert notifications. In one embodiment, the processes are performed by processing logic that may comprise hardware (circuitry, dedicated logic, etc.), software (e.g., software running on a chip), firmware, or a combination of the three. In one embodiment, the process is performed automatically by a system having an AI engine and a device with a display to receive and display an alert notification.

Referring to FIG. 8, the process begins by processing logic sending an indication (e.g., message(s), signal(s), command(s), etc.) to the AI engine that the medical image has been received by a medical information management system and is available for analyzing by the AI engine (processing block 801). In one embodiment, the indication is sent by the medical image management system (e.g., a PACS or other medical image repository, Fujifilm Synapse, etc.) in response to receiving a medical image from a modality. In another embodiment, the indication is sent by a modality that generates and sends the image. Such an indication may be sent at the same time the image is sent to a medical image management system or at a predetermined time after the medical image is send to the medical image management system.

In response to receiving the indication, processing logic determines whether one or more features in a medical image of a patient meet predefined criteria and optionally other information (e.g., information related to the medical condition), where the predefined criteria is indicative of a medical condition (processing block 802). In one embodiment, the determination is performed by the AI engine. In one embodiment, the one or more features include one or more of anatomical features and abnormalities set forth in the medical image. In one embodiment, the AI engine determines whether the one or more features in the medical image meet the predefined criteria without user input in the decision making process as to whether the one or more features in a medical meet the predefined criteria.

In one embodiment, the predefined criteria comprise a formula that includes the one or more features as inputs. Such a formula may have other inputs that are not from the features of the medical image. The data for these inputs may be obtained from sources external to the medical image and/or the AI engine. For example, such data inputs may include information from one or more medical records, test results, or other medical images of the patient.

In one embodiment, the optional, other information comprises one or more of a group consisting of: a DICOM image, an HL7 report, a medical record, other information specified by a doctor or other medical professional, Vendor Neutral Archive (VNA), etc. Once a determination has been made that the features of the medical image meet predetermined criteria, processing logic determines whether an alert notification is to be sent (processing block 803). In one embodiment, the alert notification is regarding the results of determining whether the one or more features in the medical image meet the predefined criteria.

If an alert notification is to be sent, processing logic selects the indicia indicative of the priority level to use for the notification based on an urgency with respect to the medical condition of the patient (processing block 804). Various indicia may be used to set forth the priority level to the viewer of the notification. For example, in one embodiment, different colors are used in the alert notification to specify different levels of urgency (e.g., red equals very urgent, while green equals no urgency). In another embodiment, different types and/or sizes of icons or other graphical interface display elements (e.g., icons) may be used to convey different priority levels. For example, if certain criteria are met, processing logic may determine that the medical condition of the patient is grave and based on that an urgent priority level is selected for the alert notification. In such a case, the urgent priority level may be indicated through the use of a visual indicator (e.g., a particular display icon, red color, etc.). In another embodiment, the alert notification may or may not include an audio indicator to specify different priority levels. Alternatively, different audio alerts may be used to represent different levels of priority.

After selecting the priority level, processing logic sends the alert notification with the indicia indicative of the priority level (if the one or more features in the medical image meet the predefined criteria), and includes medical information that prompted the sending of the notification at the priority level (processing block 805). In one embodiment, the medical information is indicative of the findings made by the AI engine. In one embodiment, such findings include a medical rationale that prompted sending the notification at the particular priority level used in the notification. In one embodiment, the medical information includes a portion of the medical image that is relevant to the criteria. The particular portion may be an image slice (e.g., a snapshot). In one embodiment, the image slide includes highlighted material or additions made to highlight specific portions of the image that are relevant to the findings or medical rationale used or conclusion made by the AI engine.

Processing logic presents the alert notification in a display (processing block 806). In one embodiment, the alert notification is presented in a work list on a computing device that includes a display screen. The work list may be shown in a portion of a browser interface generated by running medical software running on a client computer system that generates and displays the work list on its display. In another embodiment, the alert notification is presented in a chat window. In one embodiment, the chat window enables bidirectional communication between one or more individuals and a remote location, including, but not limited to, the AI engine, a hospital or a medical facility. In yet another embodiment, the alert notification in sent to a mobile device through which information related to the notification is accessible. In such a case, the alert notification prompts an individual to access the medical data and/or images that are related to and/or caused the alert notification to be generated.

An Exemplary Medical Imaging Management System

Figure 9:
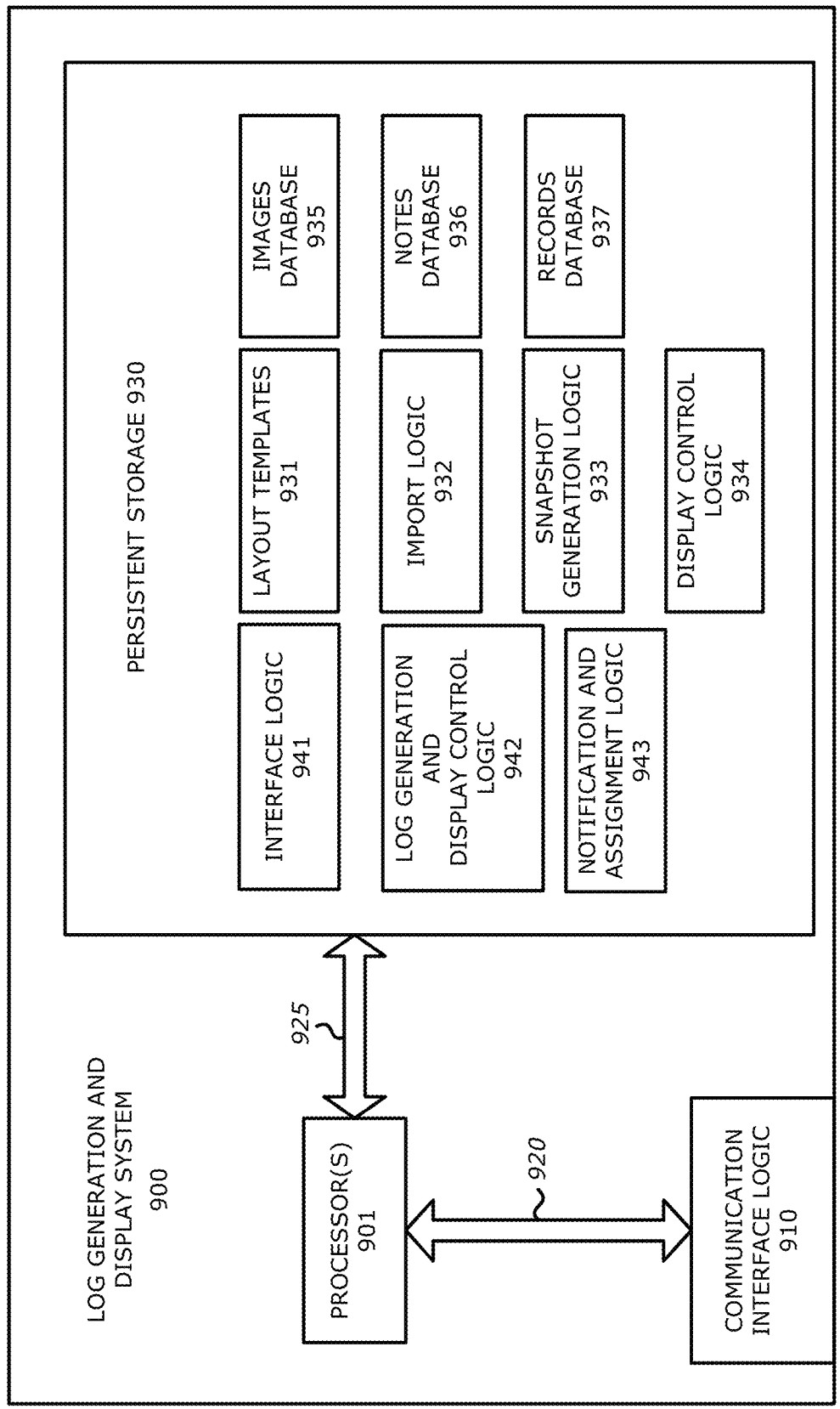
FIG. 9 illustrates an exemplary embodiment of a logical representation of a log generation and display system.

FIG. 9 illustrates an exemplary embodiment of a logical representation of a log generation and display system 900 that generates and renders the logs discussed above. The system generates individual log entries that can have snapshots. In one embodiment, system 900 is part of a medical image system such as detailed above. Although not shown, in one embodiment, such a medical image management system has, or is in communication with an AI engine.

The log generation and display system 900 includes one or more processors 901 that are coupled to communication interface logic 910 via a first transmission medium 920. The communication interface logic 910 enables communications with other electronic devices, specifically enabling communication with remote users such as doctors, nurses and/or medical technicians. According to one embodiment of the disclosure, communication interface logic 910 may be implemented as a physical interface including one or more ports for wired connectors. Additionally, or in the alternative, communication interface logic 910 may be implemented with one or more radio units for supporting wireless communications with other electronic devices.

The processor(s) 901 is further coupled to persistent storage 930 via transmission medium 925. According to one embodiment of the disclosure, persistent storage 930 may include (a) user interface logic 941, (b) log generation and display control logic 942, (c) notification and assignment logic 943, (d) the layout templates 931, (e) an import logic 932, (f) a snapshot generation logic 933, (g) a display control logic 934, (h) an images database 935, (i) a notes database 936 and (j) a records database 937.

The user interface logic 941 may include logic for enabling interaction between a user and the display areas being displayed on the screen.

The log generation and display control logic 942 includes logic for controlling the generation of a log, such as a thinklog, including generating log entries and storing a log with a study, as well as control logic to handle interaction with a log such as, for example, sorting log entries, searching log entries, assigning types to log entries, determining which log entries are to be displayed.

The notification and assignment logic 943 includes logic to issue and send notifications and/or assignments for study (and log) reviews. In one embodiment, notification and assignment logic 943 sends alert notifications.

The import logic 932 may include logic for retrieving one or more pieces of information from a storage device and importing each of the one or more pieces of information into a separate display area of a layout template. For example, the pieces of information may include, but are not limited or restricted to, (i) medical images, including x-rays, mammograms, computerized tomography (CT) scans, magnetic resonance imaging (MRI), positron emission tomography (PET) scan and/or ultrasound imaging, (ii) physician's notes regarding one or more of the medical images and/or (iii)

medical records corresponding to one or more of the subjects of the one or more medical images.

The snapshot generation logic 933 may include logic for saving at least a first state of the layout template. Saving the first state may include storing, at least, (i) the one or more pieces of information, and (ii) viewing properties of each of the one or more pieces of information in a non-transitory computer-readable medium. The display control logic 934 may include logic for retrieving one of a set of saved states of the layout template for display according to a selection of a user and displaying (e.g., rendering a display screen) the retrieved one of the set of saved states of the layout template. Additionally, the display control logic 934 may include logic for adjusting one or more of the viewing properties according to instructions by the user (e.g., altering a brightness level, a zoom level, a contrast level, etc.). Furthermore, the display control logic 934 may include logic for stepping back in a series of adjustments made to one or more pieces of information included in a snapshot (or state thereof). In one embodiment, the display control logic 934 may, according to instructions received via the user selecting various icons on the display screen, step back to previous states based on adjustments to one or more viewing properties.

For example, assume a doctor had increased the brightness level from 100% to 150% and then increased the zoom level from to focus on a particular aspect of the medical image before saving the state of the layout as a first state of a snapshot and closed the display screen. Upon opening the first state of the snapshot, the doctor (or another user) would see the medical image at a brightness level of 150% and at the increased zoom level focusing on the particular aspect of the medical image. The doctor may then step back to previous states based on the adjustments to the medical image that were previously made. Therefore, the doctor may step back to a normal zoom level and subsequently step back to a brightness level of 100%. Additionally, the doctor may be able to return to the initial state of the medical image, step forward, assuming a step back has been taken and/or step forward to the state when the first state was saved. Of course, when implemented as hardware, one or more of these logic units could be implemented separately from each other.

The images database 935, the notes database 936 and the records database 937 may comprise a single non-transitory computer-readable medium storage device or may each be a separate non-transitory computer-readable medium storage device. In one embodiment, each of the databases 935-937 may take the form of a hash table on a single non-transitory computer-readable medium storage device. The images database 935 stores medical images that a user may import into a display area of a layout template. The notes database 936 stores notes recorded by a doctor, nurse, medical technician, etc., that a user may import into a display area of a layout template. Finally, the records database 937 stores medical records that a user may import into a display area of a layout template.

In one embodiment, the AI engine sends alert notifications to a specific type of doctor (e.g., a neurologist) who is on duty. In such a case, in one embodiment, the alert notification is sent to the doctor's personal computing device (e.g., smart phone, laptop computer, etc.). In another embodiment, the AI engine sends alert notifications to a family/personal physician who is alerted anytime their client is admitted to any hospital in the world running or having access to the AI engine.

In one embodiment, an AI engine, such as described above, is able to access and/or make use of the log generation system, including the snapshot generation logic, to create log and chat entries with alert notifications and their associated information.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. A computer-implemented method comprising:
analyzing, by one or more processors executing an image analysis engine, a medical image of a patient, based on automatically obtaining the medical image of the patient from an image repository, responsive to the image being saved in the image repository, wherein the medical image is of a given image type;
determining, by the one or more processors, based on analyzing the medical image of the patient with the image analysis engine, that one or more features in the medical image of the patient meet predefined criteria, the predefined criteria being indicative of a medical condition, wherein the determining comprises:
locating, by the one or more processors, a portion of the medical image comprising one or more aspects relevant to the predefined criteria; and
generating, by the one or more processors, an image slice comprising the portion of the medical image and a visual indicator of the one or more relevant aspects, wherein the determining is based on the one or more relevant aspects;
determining, by the one or more processors, that an alert notification is to be sent regarding results based on determining that the one or more features in the medical image meet the predefined criteria, wherein the determining comprises identifying medical information indicating a priority level;
sending, by the one or more processors, the alert notification with indicia indicative of the priority level based on determining that the one or more features in the medical image meet the predefined criteria, wherein the alert notification comprises the medical information and the image slice, wherein the image slice is viewable via the alert notification without viewing the medical image;
automatically generating, by the one or more processors, without human intervention, an order of one or more specific medical tests to perform on the patient, based on determining that the one or more features in the medical image meet the predefined criteria and based on comparing, in real-time, the medical image to one or more medical images of the given type, and identifying a commonality between the medical image and the one or more medical images, wherein the one or more medical images are medical images of patients previously diagnosed with the medical condition; and
sending the order for the one or more specific medical tests with the alert notification or sending the order to a medical facility to administer or cause performance of the one or more specific medical tests.

2. The method of claim 1, wherein the medical information indicating the priority level comprises-a medical rationale for the priority level.

3. The method of claim 1, wherein determining whether the criteria are met is also based on other information related to the medical condition.

4. The method of claim 3, wherein the other information comprises one or more of a group consisting of: a Digital Imaging and Communications in Medicine (DICOM) image, an Health Level 7 (HL7) report, and a vendor neutral archive (VNA).

5. The method of claim 1, wherein the alert notification is presented in a work list portion of a browser interface generated by running medical software.

6. The method of claim 1, wherein the alert notification is presented in a chat window.

7. The method of claim 6, wherein the chat window enables bidirectional communication between an individual and the image analysis engine.

8. The method of claim 1, wherein the alert notification in sent to a mobile device through which information related to the notification is accessible.

9. The method of claim 1, wherein the one or more features include one or more of anatomical features and abnormalities set forth in the medical image.

10. The method of claim 1, further comprising selecting the indicia indicative of the priority level based on an urgency with respect to the medical condition.

11. The method of claim 1, wherein the image analysis engine determines whether the one or more features in the medical image meet the predefined criteria without user input while determining whether the one or more features in a medical image meet the predefined criteria.

12. The method of claim 1, further comprising sending an indication to the image analysis engine that the medical image has been received by a medical information management system and is available for analyzing by the image analysis engine.

13. The method of claim 1, wherein the image analysis engine comprises an artificial intelligence (AI) engine.

14. A computer program product comprising:
a non-transitory computer readable storage medium readable by one or more processors and storing instructions for execution by the processor for performing a method comprising:
analyzing, by the one or more processors executing an image analysis engine, a medical image of a patient, based on automatically obtaining the medical image of the patient from an image repository, responsive to the image being saved in the image repository, wherein the medical image is of a given image type;
determining, by the one or more processors, based on analyzing the medical image of the patient with the image analysis engine, that one or more features in the medical image of the patient meet predefined criteria, the predefined criteria being indicative of a medical condition, wherein the determining comprises:
locating, by the one or more processors, a portion of the medical image comprising one or more aspects relevant to the predefined criteria; and
generating, by the one or more processors, an image slice comprising the portion of the medical image and a visual indicator of the one or more relevant aspects, wherein the determining is based on the one or more relevant aspects;
determining, by the one or more processors, that an alert notification is to be sent regarding results based on determining that the one or more features in the medical image meet the predefined criteria, wherein the determining comprises identifying medical information indicating a priority level;

sending, by the one or more processors, the alert notification with indicia indicative of the priority level based on determining that the one or more features in the medical image meet the predefined criteria, wherein the alert notification comprises the medical information and the image slice, wherein the image slice is viewable via the alert notification without viewing the medical image;

automatically generating, by the one or more processors, without human intervention, an order of one or more specific medical tests to perform on the patient, based on determining that the one or more features in the medical image meet the predefined criteria and based on comparing, in real-time, the medical image to one or more medical images of the given type, and identifying a commonality between the medical image and the one or more medical images, wherein the one or more medical images are medical images of patients previously diagnosed with the medical condition; and sending the order for the one or more specific medical tests with the alert notification or sending the order to a medical facility to administer or cause performance of the one or more specific medical tests.

15. The computer program product of claim 14, wherein the medical information indicating the priority level comprises a medical rationale for the priority level.

16. The computer program product of claim 14, wherein determining whether the criteria are met is also based on other information related to the medical condition.

17. The computer program product of claim 14, wherein the alert notification is presented in a work list portion of a browser interface generated by running medical software.

18. The computer program of claim 14, wherein the alert notification is presented in a chat window.

19. The computer program product of claim 14, wherein the alert notification in sent to a mobile device through which information related to the notification is accessible.

20. The computer program product of claim 14, wherein the method further comprises selecting the indicia indicative of the priority level based on an urgency with respect to the medical condition.

21. An apparatus comprising:
a memory;
one or more processors in communication with the memory; and
program instructions executable by the processor via the memory to perform a method, the method comprising:
analyzing, by the one or more processors executing an image analysis engine, a medical image of a patient, based on automatically obtaining the medical image of the patient from an image repository, responsive to the image being saved in the image repository, wherein the medical image is of a given image type;
determining, by the one or more processors, based on analyzing the medical image of the patient with the image analysis engine, that one or more features in the medical image of the patient meet predefined criteria, the predefined criteria being indicative of a medical condition, wherein the determining comprises:
locating, by the one or more processors, a portion of the medical image comprising one or more aspects relevant to the predefined criteria; and
generating, by the one or more processors, an image slice comprising the portion of the medical image and a visual indicator of the one or more relevant aspects, wherein the determining is based on the one or more relevant aspects;
determining, by the one or more processors, that an alert notification is to be sent regarding results based on determining that the one or more features in the medical image meet the predefined criteria, wherein the determining comprises identifying medical information indicating a priority level;
sending, by the one or more processors, the alert notification with indicia indicative of the priority level based on determining that the one or more features in the medical image meet the predefined criteria, wherein the alert notification comprises the medical information and the image slice, wherein the image slice is viewable via the alert notification without viewing the medical image;
automatically generating, by the one or more processors, without human intervention, an order of one or more specific medical tests to perform on the patient, based on determining that the one or more features in the medical image meet the predefined criteria and based on comparing, in real-time, the medical image to one or more medical images of the given type, and identifying a commonality between the medical image and the one or more medical images, wherein the one or more medical images are medical images of patients previously diagnosed with the medical condition; and
sending the order for the one or more specific medical tests with the alert notification or sending the order to a medical facility to administer or cause performance of the one or more specific medical tests.

22. The apparatus of claim 21, wherein the medical information indicating the priority level comprises a medical rationale for the priority level.

23. The apparatus of claim 21, wherein the image analysis engine is operable to determine whether the criteria are met based additionally on other information related to the medical condition.

24. The apparatus of claim 21, wherein the alert notification is presented in a work list portion of a browser interface generated by running medical software.

25. The apparatus of claim 21, wherein the alert notification is presented in a chat window.

26. The apparatus of claim 21, wherein the alert notification in sent to a mobile device through which information related to the notification is accessible.

27. The apparatus of claim 21, wherein the image analysis engine is operable to select the indicia indicative of the priority level based on an urgency with respect to the medical condition.

28. The apparatus of claim 21, wherein the image analysis engine comprises an Artificial Intelligence (AI) engine.

* * * * *